United States Patent [19]
Johnson et al.

[11] Patent Number: 5,286,752
[45] Date of Patent: Feb. 15, 1994

[54] ANTIARRHYTHMIC DIARYLAMIDINES

[75] Inventors: Robert E. Johnson, East Greenbush; Thomas E. D'Ambra, North Greenbush, both of N.Y.

[73] Assignee: Sterling Winthrop Inc., New York, N.Y.

[21] Appl. No.: 757,083

[22] Filed: Sep. 10, 1991

[51] Int. Cl.$^5$ .................. A61K 31/155; C07C 257/18
[52] U.S. Cl. .................................. 514/637; 514/821; 564/244; 564/247
[58] Field of Search ............... 564/244, 247; 514/637, 514/821

[56] References Cited

U.S. PATENT DOCUMENTS 3,862,228  1/1975  Rodriguez et al. ............. 260/564 R
4,072,675  2/1978  Wu et al. ........................... 564/247

OTHER PUBLICATIONS

Marchand-Brynaert et al. "2-amino-1-azetines, etc." *J.C.S. Chem Comm.* (1980) 173-4.
Meyer, H. J. et al. "Studies on Organophosphorous Compounds XIV. HMPA-Induced Rearrangements of N-Benzyl-Carboxamides into 3-Phenylpropionitriles" *Bull. Soc. Chim. Belg.* 84:735-739 (1975).
Winthrop, S. O. et al. "New Analeptics: 1-(Diphenylmethyl)-2-methyl-2-thiopseudourea Analogs" *J. Org. Chem.* 24: 1936-1939 (1959).
The Registry of Toxic Effects of Chemical Substances, Record No. 37022 (1989).
Reynaud, P. et al. "Échange d'ammoniac dans les amidines par réaction avec les amines: Mécanisme et application à la préparation d'amidines mono et $N,N'$-disubstituees" *Bull. Soc. Chim. Fr.* 1978 part II: 449-456.
Wicherink, S. C. et al. "Synthesis of Tetrasubstituted Formamininium Salts Containing Different $N$-Alkyl Substituents" *Synthesis* 1977:273-275.
Adams, R. et al. "Action of the Grignard Reagent on CN Compounds. Synthesis of Amidines from Cyanamides" *J. Am. Chem. Soc.* 38:2768-2772 (1916).
Kato, T. et al. "Studies on Ketene and Its Derivatives LV Reaction of Primary Amine with Ketene Acetals" *Yakagaku Zasshi* 93:1034-1042 (1973).
Garmaise D. L. et al. "Bacteriostats V The Preparation and Bacteriostatic Properties of Amidine Derivatives" *Can. J. Chem.* 39:1493-1501 (1961).

*Primary Examiner*—Richard L. Raymond
*Assistant Examiner*—P. O'Sullivan
*Attorney, Agent, or Firm*—Michael D. Alexander; Paul E. Dupont

[57] ABSTRACT

Novel diarylamidines, and compositions and methods for treating cardiac arrhythmias in mammals utilizing the novel and related known diarylamidines of formula I, II, III and IV

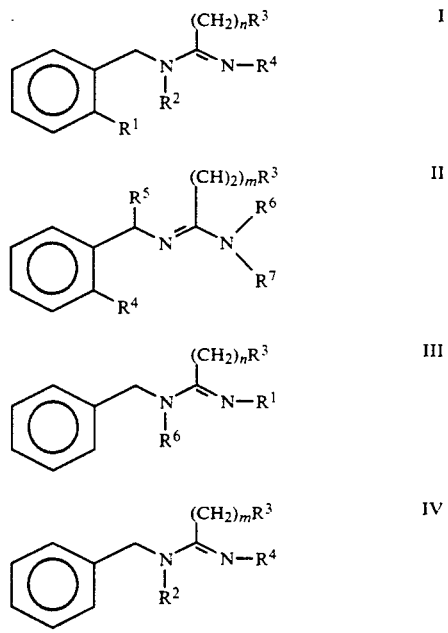

9 Claims, No Drawings

ANTIARRHYTHMIC DIARYLAMIDINES

BACKGROUND OF THE INVENTION

1. Field of the Invention

The present invention relates to novel diarylamidines, and to compositions and methods for treating cardiac arrhythmias in mammals utilizing the novel and related known diarylamidines.

2. Information Disclosure Statement

Meyer et al. [*Bull. Soc. Chim. Belg.* 84, 735-739 (1975)] disclose N'-(diphenylmethyl)-N,N-dimethylethanimidamide. No utility is disclosed.

Marchand-Brynaert et al. (*J. C. S. Chem. Comm.*, 1980, 173-174) disclose N'-(diphenylmethyl)-N,N-dimethylbenzenepropanimidamide. No utility is disclosed.

Winthrop and Gavin [*J. Org. Chem.* 24, 1936-1939 (1959)] disclose N'-(diphenylmethyl)ethanimidamide and N'-(diphenylmethyl)propanimidamide. They state that "the amidines and guanidines were convulsants at high doses".

The Registry of Toxic Effects of Chemical Substances, available on-line from the National Institute of Occupational Safety and Health, lists a chemical structure for N'[(4-chlorophenyl)phenylmethyl]-N,N-dimethylmethanimidamide. An $LD_{50}$ is given, but no other information on its preparation or utility is disclosed.

Reynaud et al (*Bull. Soc. Chim. Fr.* 1978 part II, 449-456) disclose N,N'-bis(phenylmethyl)ethanimidamide and N,N'-bis(phenylethyl)benzenethanimidamide. No utility is disclosed.

Wicherink et al. (*Synthesis* 1977, 273-275) disclose N-methyl-N,N'bis(phenylmethyl)methanimidamide. No utility is disclosed.

Rodriguez and deStevens U.S. Pat. No. 3,862,228 disclose N-[(3,4-dimethoxyphenyl)methyl]-4-methylbenzeneethanimidamide as a hypoglycemic and diuretic agent.

Adams and Beebe [*J. Am. Chem. Soc.* 38, 2768-2772 (1916)] disclose N,N-bis(phenylmethyl)propanimidamide. No utility is disclosed.

Kato et al. [*Yakagaku Zasshi* 93, 1034-1042, (1973) (*Chem. Abstr.* 79:105053d] disclose N,N'-bis(phenylmethyl)propanimidamide.

Garmaise et al. [*Can. J. Chem* 39, 1493-1501 (1961)] discloses N-[(3,4-dichlorophenyl)methyl]3,4-dichlorobenzeneethanimidamide as an antibacterial agent.

SUMMARY OF THE INVENTION

In a product aspect, the invention relates to compounds of formulas I, II and III

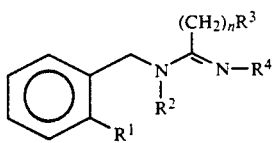

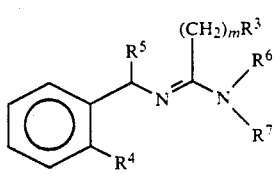

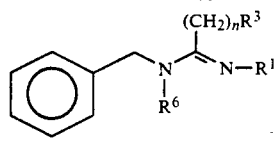

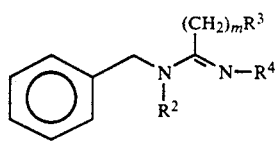

wherein $R^1$ is benzyl or benzyl substituted on the aromatic ring with a substituent chosen from the group consisting of lower-alkyl, lower-alkoxy and halogen;

$R^2$ is hydrogen, lower-alkyl or benzyl;

$R^3$ is hydrogen, phenyl, or phenyl substituted with lower-alkyl, lower-alkoxy or halogen;

$R^4$ is hydrogen, lower-alkyl, benzyl, or benzyl substituted with lower-alkyl, lower-alkoxy or halogen;

$R^5$ is phenyl or phenyl substituted with lower-alkyl, lower-alkoxy or halogen;

$R^6$ and $R^7$ are independently lower-alkyl;

m is zero, 1, 2, or 3;

n is 1, 2 or 3;

with the proviso that in formula II, when $R^4$ is hydrogen and both of $R^6$ and $R^7$ are methyl, the following three combinations are excluded: (1) $R^3$ is hydrogen, $R^5$ is phenyl and m is one, (2) $R^3$ and $R^5$ are phenyl and m is two, (3) R3 is hydrogen, $R^5$ is 4-chlorophenyl and m is zero.

Preferred compounds are those of formula I wherein $R^1$ is benzyl, $R^2$ is hydrogen or lower-alkyl and $R^4$ is hydrogen. Also preferred are compounds of formula II as discribed above further resticted in that $R^1$ is hydrogen, $R^5$ is phenyl, and $R^6$ and $R^7$ are methyl.

Particularly preferred are those of formula I wherein $R^1$ and $R^3$ are hydrogen, $R^2$ is methyl, $R^4$ is benzyl and n is two; or wherein $R^1$ is benzyl, $R^2$ is hydrogen or methyl, $R^3$ and $R^4$ are hydrogen, and n is two; compounds of formula II wherein $R^1$ and $R^3$ are hydrogen, $R^6$ and $R^7$ are methyl, $R^5$ is phenyl and m is zero; and compounds of formula III wherein $R^1$ is benzyl, $R^3$ is hydrogen, $R^6$ is methyl and n is two.

In a method aspect, the invention relates to a method for the treatment of cardiac arrhythmia in a patient in need of such treatment which comprises administering an antiarrhythmically effective amount of a compound of structure I, II, III or IV wherein $R^1$ is benzyl or benzyl substituted on the aromatic ring with a substituent chosen from the group consisting of lower alkyl, lower-alkoxy and halogen;

$R^2$ is hydrogen, lower-alkyl or benzyl;

$R^3$ is hydrogen, phenyl, or phenyl substituted with lower-alkyl, lower-alkoxy or halogen;

$R^4$ is hydrogen, lower-alkyl, benzyl, or benzyl substituted with lower-alkyl, lower-alkoxy or halogen;

$R^5$ is phenyl or phenyl substituted with lower-alkyl, lower-alkoxy or halogen;

$R^6$ and $R^7$ are independently lower alkyl;

m is zero, 1, 2 or 3;

n is 1, 2 or 3;

with the proviso that in formula IV at least one of $R^2$, $R^3$ and $R^4$ must contain an aromatic ring.

In a composition aspect, the invention relates to a composition for the treatment of cardiac arrhythmia comprising a pharmaceutical carrier and an antiarrhythmically effective amount of a compound of structure I, II, III or IV wherein $R^1$ is benzyl or benzyl substituted on the aromatic ring with a substituent chosen from the group consisting of lower alkyl, lower-alkoxy and halogen;

$R^2$ is hydrogen, lower-alkyl or benzyl;

$R^3$ is hydrogen, phenyl, or phenyl substituted with lower-alkyl, lower-alkoxy or halogen;

$R^4$ is hydrogen, lower-alkyl, benzyl, or benzyl substituted with lower-alkyl, lower-alkoxy or halogen;

$R^5$ is phenyl or phenyl substituted with lower-alkyl, lower-alkoxy or halogen;

$R^6$ and $R^7$ are independently lower alkyl;

m is zero, 1, 2 or 3;

n is 1, 2 or 3;

with the proviso that at least one of $R^2$, $R^3$ and $R^4$ must contain an aromatic ring.

It should be noted that in the case wherein $R^2$ is hydrogen, the compounds exist as tautomers and both tautomers are intended to be comprehended by structure I:

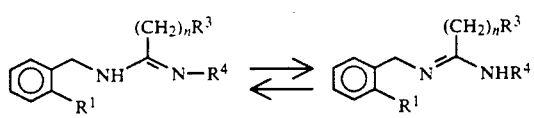

Lower-alkyl as used herein describes linear, branched, or cyclic saturated carbon chains of six or fewer carbon atoms; lower-alkoxy as used herein describes linear or branched alkoxy substituents containing six or fewer carbon atoms; halogen describes bromine, chlorine or fluorine.

In the text that follows, the substituents R are defined when initially presented and maintain that definition whenever they occur subsequently.

DETAILED DESCRIPTION INCLUSIVE OF PREFERRED EMBODIMENTS

The compounds of the invention may be synthesized by procedures well known in the art for the synthesis of amidines. Although many methods are possible (see Patai *The Chemistry of Amidines and Imidates*, Wiley and Sons, New York, 1975, p. 283-348 which is incorporated herein by reference), we have found the condensation of iminoethers or amide acetals with amines to be well suited to the production of compounds of the invention:

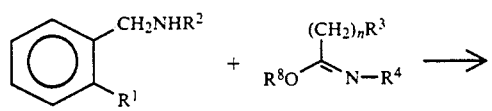

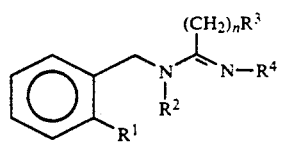

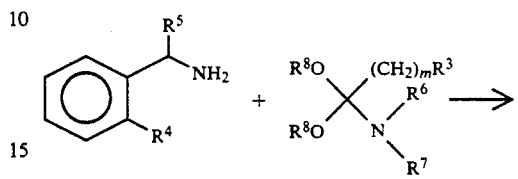

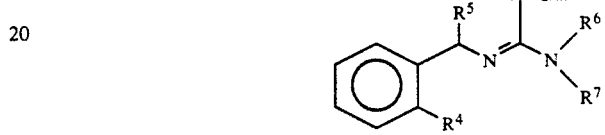

wherein $R^8$ is lower-alkyl, preferably methyl or ethyl.

In some cases suitably substituted 2,4-benzodiazepines were available, and these were hydrogenolyzed to provide compounds of formula VI (formula I wherein $R^4$ is hydrogen):

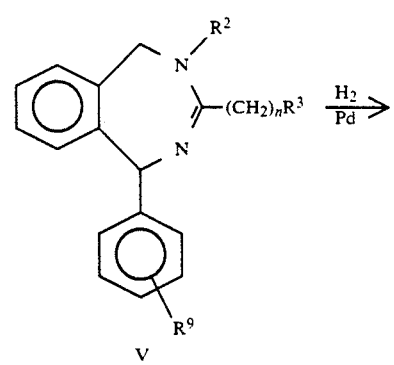

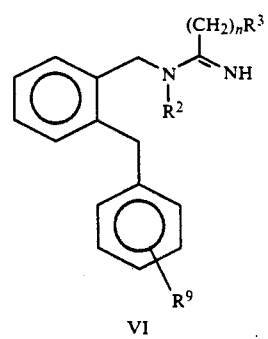

wherein $R^9$ is lower-alkyl, lower-alkoxy or halogen.

The benzodiazepines of formula V are available from the appropriate benzoylbenzoic acids via the following route:

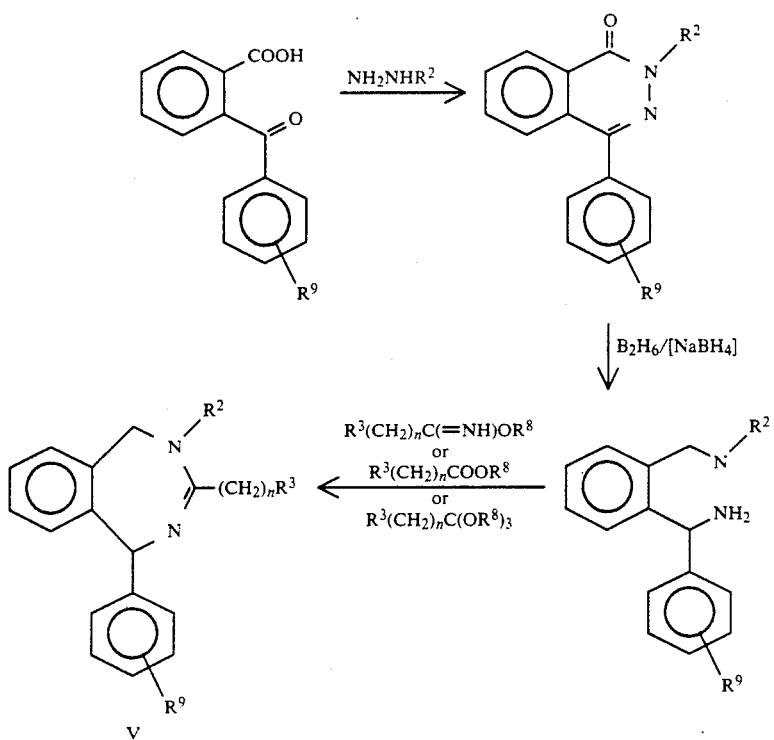

V

A suitably substituted 2-benzoylbenzoic acid is reacted with a hydrazine in an inert solvent, preferably toluene, to provide a phthalazinone which is reduced to the diamine with a large excess (3.5 to 9 equivalents) of diborane in an inert solvent, preferably THF, at 20°–100°, preferably at reflux. When the reduction is sluggish, a catalytic amount of sodium borohydride and some diglyme may be added.

The diamine may be condensed in one of three ways to produce the benzodiazepine: (1) the free base of the diamine in acetic acid is treated with five to seven equivalents of the appropriate orthoester $R^3(CH_2)_nC(OR^8)_3$ at 0°–50° C., preferably 25° C, or the diacid salt of the diamine, preferably the dihydrochloride salt, in an inert solvent is treated with five to seven equivalents of an appropriate orthoester plus one to two equivalents of a weak base, preferably sodium or potassium acetate; (2) a diacid salt of the diamine, preferably the dihydrochloride salt, in an inert solvent, preferably methanol, is treated with two to three equivalents of the appropriate iminoether hydrochloride and about two equivalents of a weak base, preferably sodium acetate, at 0°–60° C., preferably 25° C., or the free base of the diamine in an inert solvent, preferably methanol, is treated with two to three equivalents of the appropriate iminoether hydrochloride and two to three equivalents of a weak acid, preferably acetic acid, at 0°–60° C., preferably 25° C., or (3) a diamine or a diacid salt of the diamine, preferably the dihydrochloride salt, in an inert solvent, preferably toluene, is treated with slightly more than two equivalents of trimethylaluminum at −30° to +110° C., followed by treatment with 1 to 1.5 equivalents of a lower-alkyl ester of the appropriate acid $[R^3(CH_2)_nCOOR^8]$.

It will be noted that compounds of the invention of formula II may be asymmetric at the carbon adjacent $R^5$ in some cases. In those cases there may be an advantage to using one or the other enantiomer for the treatment of arrhythmia. Single enantiomers may be synthesized from chiral starting materials or the racemates may be resolved by methods well known in the art, such as chromatography on chiral media or recrystallization of diastereomeric salts.

The compounds of the invention are useful both in the free base form and the form of acid-addition salts, and both forms are within the purview of the invention. The acid-addition salts are in some cases a more convenient form for use, and in practice the use of the salt form inherently amounts to the use of the base form. The acids which can be used to prepare the acid-addition salts include preferably those which produce, when combined with the free base, medicinally acceptable salts, that is, salts whose anions are relatively innocuous to the animal organism in medicinal doses of the salts so that the beneficial properties inherent in the free base are not vitiated by side effects ascribable to the anions. In practicing the present invention, it is convenient to form the hydrochloride, fumarate, toluenesulfonate, hydrogen sulfate, methanesulfonate, or maleate salts. However, other appropriate medicinally acceptable salts within the scope of the invention are those derived from other mineral acids and organic acids. The acid-addition salts of the basic compounds are prepared either by dissolving the free base in aqueous alcohol solution containing the appropriate acid and isolating the salt by evaporating the solution, or by reacting the free base and an acid in an organic solvent, in which case the salt separates directly, is precipitated with a second organic solvent, or can be obtained by concentration of the solution. Although medicinally acceptable salts of the basic compounds are preferred, all acid-addition salts are within the scope of the present invention. All acid-addition salts are useful as sources of the free base form even if the particular salt per se is desired only as an intermediate product, as, for example, when the salt is formed only for purposes of purification or identification, or when it is used as an intermediate in preparing a medicinally acceptable salt by ion exchange procedures.

The structures of the compounds of the invention were established by the mode of synthesis, by elemental analysis, and by infrared, nuclear magnetic resonance, and mass spectroscopy. The course of the reactions and the identity and homogeneity of the products were assessed by thin layer chromatography (TLC) and high-pressure liquid chromatography (HPLC). The starting materials are either commercially available or may be prepared by procedures well known in the art.

In the following procedures, melting points are given in degrees C and are uncorrected.

In the examples which follow, Me is methyl, Et is ethyl, Ph is phenyl, Bzl is benzyl, iPr is isopropyl, tBu is t-butyl, OAc is acetyl, THF is tetrahydrofuran, hex is hexane, IPA is isopropylamine, DMF is dimethylformamide, and TMS is trimethylsilyl.

EXAMPLE 1

N-Methyl-N,N'-bis(phenylmethyl)propanimidamide
(III: $R^1$=Bzl, $R^3$=H, $R^6$=Me, n=2)

A solution of 8.15 g (50 mmol of N-benzylpropanamide in 100 mL of methylene chloride under nitrogen was treated with 50 mL of 1 M triethyloxonium fluoroborate. The mixture was stirred at room temperature or 22 hours, partially stripped and poured into 800 mL of ether. The ether was decanted from the resulting oil, the oil was triturated with hexane, the hexane decanted and the residue of 11.6 g of oil was used without further purification.

The oily ethoxyiminium salt was combined with 7.6 mL (59 mmol) of methylbenzylamine in 70 mL of ethanol and stirred at room temperature 24 hours. It was then heated for 2 hours at 90°, cooled to 0°, and the solid amidine was filtered off. The solid was dissolved in ethyl acetate and 1 equivalent of maleic acid in ethyl acetate was added to yield 5.1 g of product as the maleate salt, mp 116-118.

EXAMPLE 2

N-Methyl-N-[[2-(phenylmethyl)phenyl]methyl]-propanimidamide (I: $R^1$=Bzl, $R^2$=Me, $R^3$=$R^4$=H, n=2)

A mixture of 5.3 g (20 mmol) of 4,5-dihydro-3-ethyl-4-methyl-1-phenyl-1H-2,4-benzodiazepine, 1.3 g (20 mmol) of ammonium formate, and 0.6 g of 10% palladium on carbon was refluxed for 45 minutes in 120 mL of methanol. A further 1.3 g of ammonium formate was added and the mixture refluxed an additional 1.5 hours. The reaction was filtered, stripped, dissolved in methylene chloride and chromatographed on 125 g of silica gel, eluting with ethyl acetate then 2.5% triethylamine:5% methanol in methylene chloride and finally 5% triethylamine:10% methanol in methylene chloride. Approximately 2.7 g of the free base of the product was obtained from the fractions following elution with 5% triethyamine. This material was dissolved in isopropyl alcohol and treated with excess ethereal HCl. The resulting solid was filtered off and recrystallized from isopropyl alcohol/ether. After extensive drying at 100° in vacuo to remove traces of isopropyl alcohol, 2.65 g of product was obtained as the hydrochloride, mp 150-153.

EXAMPLE 3

N-[[2-(Phenylmethyl)phenyl]methyl]propanimidamide
(I $R^1$=Bzl, $R^2$=$R^3$=$R^4$=H, n=2)

By a process substantially similar to that of Example 2, 2.82 g (7.5 mmol) of 4,5-dihydro-3-ethyl-1-phenyl-4-(phenylmethyl)-1H-2,4-benzodiazepine was converted to 1.1 g of product as the hydrochloride after recrystallization from isopropyl alcohol/ether, mp 172-174.

EXAMPLE 4

N'-(Diphenylmethyl)-N,N-dimethylmethanimidamide
(II: $R^3$=$R^4$=H, $R^5$=Ph, $R^6$=$R^7$=Me, m=zero)

A solution of 9.15 g (50 mmol) of (diphenylmethyl)amine and 8.33 g (70 mmol of dimethylformamide dimethylacetal in 25 mL of dichloromethane was refluxed briefly and slowly distilled through a Vigreux column, distilling off all material that boiled at or below 90°. The residue was stripped in vacuo, poured into water, cooled, and the resulting solid filtered off. After drying, it was recrystallized from hexane to provide 8.3 g (70%) of N'-(diphenylmethyl)-N,N-dimethylmethanimidamide, mp 58-60.

EXAMPLE 5

N-(Diphenylmethyl)-N,N-dimethylethanimidamide (II: $R^3$=$R^4$=H, $R^5$=Ph, $R^6$=$R^7$=Me, m=1)

Following the procedure of Example 4, 9.15 g of (diphenylmethyl)amine and 9.3 g of dimethylacetamide dimethylacetal were converted to 9.2 g (73%) of N'-(diphenylmethyl)-N,N-dimethylethanimidamide, mp 68'70 from hexane.

EXAMPLES 6-10

By a procedure analogous to that of Example 1, it is contemplated that the following amines and iminoethers may be converted to the corresponding imidamides:

| Ex | $R^1$ | $R^2$ | $R^3$ | $R^4$ | n |
|---|---|---|---|---|---|
| 6 | Me | Bzl | Ph | sec-$C_4H_9$ | 2 |
| 7 | H | $nC_6H_{13}$ | 4-(Meo)Ph | H | 1 |
| 8 | Bzl | H | H | $CH_2$[4-(Cl)Ph] | 1 |
| 9 | Bzl | iPr | 3-(Cl)Ph | cyclo-$C_5H_9$ | 1 |
| 10 | 4-(Cl)Bzl | Me | H | $nC_4H_9$ | 3 |

EXAMPLES 11-13

By a procedure analogous to that of Example 2, it is contemplated that the following benzodiazepines may be hydrogenolyzed to provide the corresponding imidamides:

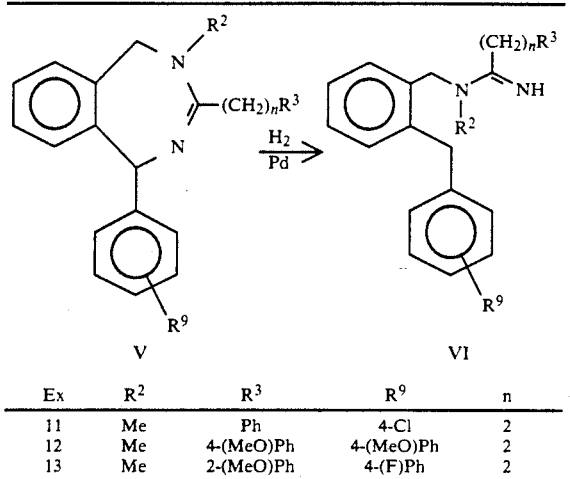

| Ex | $R^2$ | $R^3$ | $R^9$ | n |
|----|-------|-------|-------|---|
| 11 | Me | Ph | 4-Cl | 2 |
| 12 | Me | 4-(MeO)Ph | 4-(MeO)Ph | 2 |
| 13 | Me | 2-(MeO)Ph | 4-(F)Ph | 2 |

EXAMPLE 14

By a procedure analogous to that of Example 4, it is contemplated that 2-methyl-(α-phenylbenzenemethanamine [Cervinka et al. Coll. Czech. Chem. Comm. 30, 2484-2487 (1965)] and the dimethylacetal of N-hexyl-N-methylbutamide may be reacted to provide N-hexyl-N-methyl-N'-[(2-methylphenyl)(phenyl)methyl]-butanimidamide (II: $R^4=R^6=Me$, $R^3=H$, $R^5=Ph$, $R^7=nC_6H_{13}$, m=3).

The compounds of this invention having formulas I, II, III and IV have antiarrhythmic activity as shown by the results of standard pharmacological tests carried out on representative examples as described below.

Antiarrhythmic activity was demonstrated by a procedure, which is a modification of standard programmed electrophysiological techniques utilized in large animals and in clinical studies in humans. Male Duncan-Hartley guinea pigs (600-800 grams) were anesthetized with sodium pentobarbital (30 mg/kg, i.p.) and artificially ventilated with a Harvard small-animal respirator. A left thoracotomy was performed and a animal respirator. A left thoracotomy was performed and a fluid-filled catheter and transducer (Millar Microtip, Model 4F, Millar Inst. Inc., Houston, Texas) were inserted through the anterior wall of the left ventricle to monitor left ventricular pressure (LVP). The first derivative of the LVP (dP/dt) was obtained from a Grass differentiator (Model 7P20B) and used as an index of contractile function. A lead II EKG along with LVP and dP/dt were continuously recorded on a Grass polygraph (Model 7B). Rate pressure product (RPP), an index of cardiac work, was calculated using peak systolic LVP and heart rate (HR).

Effective refractory periods (ERP) were evaluated during left ventricular pacing. Grass subcutaneous electrodes were implanted as bipolar ventricular electrodes to deliver stimuli from a Bloom DTU-2 stimulator (Bloom Electronics, Inc., Reading, Pa.) and stimulus isolation unit. Hearts were stimulated at the slowest frequency allowing consistent pacing (S1, 240-300 bpm) using 2 ms pulses at twice diastolic threshold. Threshold was determined by increasing the stimulation voltage until a 1:1 capture of the ventricular response with the stimulus was observed. A train of 8 normal pulses was delivered followed by a premature (S2) pulse. The interval between the last S1 and the premature S2 pulse was reduced in 10-ms increments until a ventricular response was not initiated. The longest S1-S2 interval that failed to produce a ventricular response was defined as the ERP. Pacing stimuli and the EKG were displayed at a sampling frequency of 92 Hz on an Apple IIe microcomputer using a two-channel 8-bit A/D converter (R.C. Electronics, Compu-Scope APL-D2, Santa Barbara, Calif.).

Baseline hemodynamic function was evaluated followed by ventricular pacing to determine ERP. Pacing was discontinued prior to drug administration and resumed at set intervals during the protocol to evaluate ERP. Test compounds were administered (1 mL/kg) via the left ventricular catheter over a 15-second interval for doses less than 10 mg/kg. Higher doses (>10 mg/kg) were slowly infused over a 1-minute interval. Doses were cumulatively increased every 15 minutes until a maximally tolerated dose which reduced dP/dt by 50% was noted. Ten minutes after each dose, hemodynamics and ERP were reevaluated.

Data were analyzed using an analysis of variance for repeated measures of raw data and are expressed as means. An effective dose to increase ERP by a minimum of 20 msecs ($ED_{20}$), which was consistently a statistically significant increase, was derived for each animal from a linear regression of the data and expressed as a mean for the treated population. Biological significance was established at a probability of error less than 0.05. The results are presented in Table A.

| Example | $ED_{20}$ mg/kg |
|---------|-----------------|
| 1 | 0.42 |
| 2 | 1.3 |
| 3 | 1.3–9.8 |
| 4 | 29.7 |
| 5 | 2.6–3.0 |

The pharmaceutical compositions of the present invention include one or more of the compounds of this invention formulated into compositions together with one or more nontoxic physiologically acceptable carriers, adjuvants or vehicles which are collectively referred to herein as carriers, for parenteral injection, for oral administration in solid or liquid form, for rectal or topical administration, and the like.

The compositions can be administered to humans and animals either orally, rectally, or parenterally (intravenously, intramuscularly or subcutaneously).

Compositions suitable for parenteral injection may comprise physiologically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethyleneglycol, glycerol and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents for example sugars, sodium chloride and the like. Prolonged absorption of the injectable pharmaceutical form can be brought about by the use of agents delaying absorption; for example, aluminum monostearate and gelatin.

Solid dosage forms for oral administration include capsules, tablets, pills, powders and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol and silicic acid, (b) binders, as for example, carboxymethylcellulose, alginates, gelatin, polyvinylpyrrolidone, sucrose and acacia, (c) humectants, as for example, glycerol, (d) disintegrating agents, as for example, agar-agar, calcium carbonate, potato or tapioca starch, alginic acid, certain complex silicates and sodium carbonate, (e) solution retarders, as for example, paraffin, (f) absorption accelerators, as for example, quaternary ammonium compounds, (g) wetting agents, as for example, cetyl alcohol and glycerol monostearate, (h) adsorbents, as for example, kaolin and bentonite, and (i) lubricants, as for example, talc, calcium stearate, magnesium stearate, solid polyethylene glycols, sodium lauryl sulfate or mixtures thereof. In the case of capsules, tablets and pills, the dosage forms may also comprise buffering agents.

We claim:

1. A compound chosen from the group consisting of

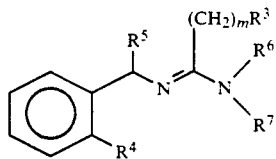

or acid-addition salts thereof wherein $R^3$ is hydrogen, phenyl, or phenyl substituted with lower-alkyl, lower-alkoxy or halogen;

$R^4$ is hydrogen, lower-alkyl, benzyl, or benzyl substituted with lower-alkyl, lower-alkoxy or halogen;

$R^5$ is phenyl or phenyl substituted with lower-alkyl, lower-alkoxy or halogen;

$R^6$ and $R^7$ are independently lower alkyl;

m is zero, 1, 2 or 3;

with the proviso that in formula II, when $R^4$ is hydrogen and both of $R^6$ and $R^7$ are methyl, the following three combinations are excluded: (1) $R^3$ is hydrogen, $R^5$ is phenyl and m is one, (2) $R^3$ and $R^5$ are phenyl and m is two, (3) $R^3$ is hydrogen, $R^5$ is 4-chlorophenyl and m is zero.

2. A compound according to claim 1 having the structure

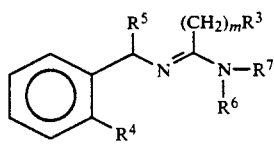

wherein $R^4$ is hydrogen, $R^5$ is phenyl and $R^6$ and $R^7$ are methyl.

3. A compound according to claim 2 wherein $R^3$ is hydrogen and m is zero.

4. A method for the treatment of cardiac arrhythmia in a patient in need of such treatment which comprises administering an antiarrhythmically effective amount of a compound of structure

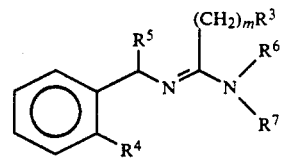

wherein $R^2$ is hydrogen, lower-alkyl or benzyl;

$R^3$ is hydrogen, phenyl, or phenyl substituted with lower-alkyl, lower-alkoxy or halogen;

$R^4$ is hydrogen, benzyl, or benzyl substituted with lower-alkyl, lower-alkoxy or halogen;

$R^5$ is phenyl or phenyl substituted with lower-alkyl, lower-alkoxy or halogen;

$R^6$ and $R^7$ are independently lower alkyl;

m is zero, 1, 2 or 3.

5. A method according to claim 4 for the treatment of cardiac arrhythmia in a patient in need of such treatment which comprises administering an antiarrhythmically effective amount of a compound of structure

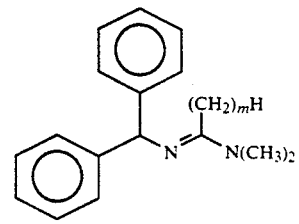

wherein m is zero or one.

6. A composition for the treatment of cardiac arrhythmia comprising a pharmaceutical carrier and an antiarrhythmically effective amount of a compound of structure

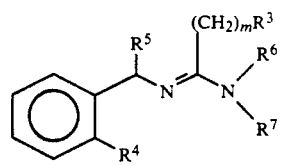

wherein $R^3$ is hydrogen, phenyl, or phenyl substituted with lower-alkyl, lower-alkoxy or halogen;

$R^4$ is hydrogen, benzyl, or benzyl substituted with lower-alkyl, lower-alkoxy or halogen;

$R^5$ is phenyl or phenyl substituted with lower-alkyl, lower-alkoxy or halogen;

$R^6$ and $R^7$ are independently lower alkyl;

m is zero, 1, 2 or 3.

7. A composition according to claim 6 for the treatment of cardiac arrhythmia comprising a pharmaceutical carrier and an antiarrhythmically effective amount of a compound of structure

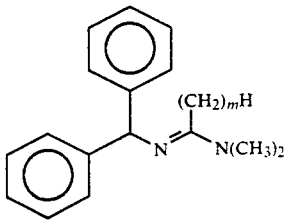

wherein m is zero or one.

8. A method for the treatment of cardiac arrhythmia in a patient in need of such treatment which comprises administering a composition according to claim 6.

9. A method for the treatment of cardiac arrhythmia in a patient in need of such treatment which comprises administering a composition according to claim 7.

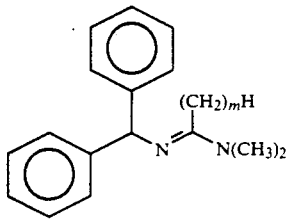

wherein m is zero or one.

8. A method for the treatment of cardiac arrhythmia in a patient in need of such treatment which comprises administering a composition according to claim 6.

9. A method for the treatment of cardiac arrhythmia in a patient in need of such treatment which comprises administering a composition according to claim 7.

* * * * *

UNITED STATES PATENT AND TRADEMARK OFFICE
CERTIFICATE OF CORRECTION

PATENT NO.  : 5,286,752

DATED       : February 15, 1994

INVENTOR(S) : Robert E. Johnson, et al.

It is certified that error appears in the above-identified patent and that said Letters Patent is hereby corrected as shown below:

Column 12, line 17, claim 4: delete the phrase "$R^2$ is hydrogen, lower-alkyl or benzyl;".

Signed and Sealed this

Sixth Day of September, 1994

Attest:

BRUCE LEHMAN

Attesting Officer

Commissioner of Patents and Trademarks